United States Patent
Kondo et al.

(10) Patent No.: US 10,787,693 B2
(45) Date of Patent: Sep. 29, 2020

(54) SINGLE-CHAIN BETA-GLUCAN COMPOSITION, METHOD FOR PRODUCING SAME, AND LIQUID COMPOSITION

(71) Applicant: ITOCHU SUGAR CO., LTD., Aichi (JP)

(72) Inventors: Nobuhiro Kondo, Aichi (JP); Katsuki Hirabayashi, Aichi (JP)

(73) Assignee: ITOCHU SUGAR CO., LTD., Aichi (JP)

( * ) Notice: Subject to any disclaimer, the term of this patent is extended or adjusted under 35 U.S.C. 154(b) by 0 days.

(21) Appl. No.: 16/062,091

(22) PCT Filed: Dec. 14, 2016

(86) PCT No.: PCT/JP2016/087157
§ 371 (c)(1),
(2) Date: Jun. 13, 2018

(87) PCT Pub. No.: WO2017/104686
PCT Pub. Date: Jun. 22, 2017

(65) Prior Publication Data
US 2018/0371515 A1 Dec. 27, 2018

(30) Foreign Application Priority Data
Dec. 14, 2015 (JP) .................................. 2015-243376

(51) Int. Cl.
| | | |
|---|---|---|
| *C12P 19/04* | (2006.01) | |
| *A61K 8/73* | (2006.01) | |
| *A23L 2/52* | (2006.01) | |
| *A61Q 19/00* | (2006.01) | |
| *A61K 8/9728* | (2017.01) | |
| *C08B 37/00* | (2006.01) | |
| *C12N 1/14* | (2006.01) | |
| *C12R 1/645* | (2006.01) | |

(52) U.S. Cl.
CPC .............. *C12P 19/04* (2013.01); *A61K 8/73* (2013.01); *A61K 8/9728* (2017.08); *A61Q 19/00* (2013.01); *C08B 37/0024* (2013.01); *C12N 1/14* (2013.01); *C12R 1/645* (2013.01); *A23L 2/52* (2013.01); *A61K 2800/10* (2013.01)

(58) Field of Classification Search
CPC ....... A23L 2/52; A61Q 19/00; C08B 37/0024; C12N 1/14; A61K 2800/10; A61K 8/9782; A61K 8/73

USPC ......................................................... 536/55.1
See application file for complete search history.

(56) References Cited

FOREIGN PATENT DOCUMENTS

| JP | 2008-138195 A | 6/2008 | |
|---|---|---|---|
| JP | 2011-103877 A | * 6/2011 | ............. C08B 37/00 |
| JP | 2011103877 A | * 6/2011 | ............. C08B 37/00 |
| JP | 2014-157504 A | 8/2014 | |

OTHER PUBLICATIONS

English Translation of International Preliminary Report on Patentability, including Written Opinion of the International Searching Authority, dated Jun. 19, 2018 in International Application No. PCT/JP2016/087157 (5 pages).
English Translation of International Search Report, dated Mar. 21, 2017 (2 pages).
Hirabayashi, K. et al., "Characterization and enzymatic hydrolysis of hydrothermally treated β-1,3-1,6-glucan from Aureobasidium pullulans," World J Microbiol Biotechnol, 32:206 (2016).
T. M. McIntire & D. A. Brant, "Observations of the (1→3)β-D-Glucan Linear Triple Helix to Macrocycle Interconversion Using Noncontact Atomic Force Microscopy," J. Am. Chem. Soc., vol. 120, pp. 6909-6919 (1998).
Nagi, N. et al., "Application of Limulus Test (G Pathway) for the Detection of Different Conformers of (1→3)-β-D-Glucans," Biol. Pharm. Bull., vol. 16(9), pp. 822-828 (1993).
Ohno, N. et al., "Corrigendum to: 'Conformation dependency of nitric oxide synthesis of murine peritoneal macrophages by (β-glucans in vitro,'" Immunology Letters, vol. 53, pp. 157-163 (1996).
Sato, et al., "Collapse of Randomly Coiled Schizophyllan in Mixtures of Water and Dimethylsulfoxide," Polymer Journal, vol. 15, No. 1, pp. 87-96 (1983).
Uryu, et al., "Sulfated alkyl aligosaccharides with potent inhibitory effects on human immunodeficiency virus infection," Biochemical Pharmacology, vol. 43, No. 11, pp. 2385-2392 (1992).
Yadomae, "Structure and Biological Activities of Fungal β-1,3-Glucans," Yakugaku Zasshi, vol. 120(5), pp. 413-431 (2000).

* cited by examiner

*Primary Examiner* — Ganapathy Krishnan
(74) *Attorney, Agent, or Firm* — McDermott Will & Emery LLP

(57) ABSTRACT

Single-chain β-glucans can be obtained by hydrothermal treatment of a solution containing (1,3)(1,6)-β-glucan for a predetermined time in a temperature range of from 145° C. to 200° C. at a pressure at or above the saturated vapor pressure at the treatment temperature. β-Glucans capable of maintaining a single-chain state for an extended period of time can be produced without chemical treatment.

15 Claims, 2 Drawing Sheets

SINGLE-CHAIN BETA-GLUCAN COMPOSITION, METHOD FOR PRODUCING SAME, AND LIQUID COMPOSITION

CROSS REFERENCE

This application is the U.S. National Phase under 35 U.S.C. § 371 of International Application No. PCT/JP2016/087157, filed on Dec. 14, 2016, which claims the benefit of Japanese Application No. 2015-243376, filed on Dec. 14, 2015, the entire contents of each are hereby incorporated by reference.

FIELD OF THE INVENTION

The present invention relates to a method for making β-glucan, which exists as a triple chain in nature, into a single chain and to a single-chain β-glucan composition. In particular, the present invention relates to a method using hydrothermal treatment for producing a composition containing a high concentration of single-chain β-glucan that is safe when ingested as a food, supplement, or the like and to a composition containing single-chain β-glucan obtained by said method.

PRIOR ART

β-glucans include polysaccharides in which glucose is linked by β1-3 bonds and polysaccharides linked by β1-4 bonds. Generally, what is referred to as a β-glucan is an ordinary β1-3 glucan. Unless noted otherwise, the description β-glucan in the present specification means a β1-3 glucan. β-glucans are polysaccharides that take on the chain structure of a triple helical structure in which hexoses are hydrogen bonded in the 1,3 direction.

β-Glucans are known to be widely distributed in nature, in plants, fungi, bacteria, and the like. β-Glucans from mushrooms such as *Agaricus, Phellinus linteus,* and *Ganoderma lucidum* and yeasts such as beer yeast, baker's yeast, and *Aureobasidium pullurans,* (common name: black yeast) are also known to have a potent immunopotentiating effect, cancer-suppressing effect, antiviral effect, and antifungal effect. They are utilized in foods, supplements, cosmetics, and the like.

Since the cell walls of yeasts such as beer yeast, baker's yeast, and *Aureobasidium* have a high β-glucan content, these yeasts are often cultured and purified. β-Glucans purified from *Aureobasidium* in particular has a strong immunopotentiating effect and a strong water-retaining effect and is therefore widely used not only in supplements but also as a food modifier, cosmetic, and the like.

*Aureobasidium* culture broth that contains β-glucans looks highly viscous, like egg white. This broth forms a gel in aqueous solution when the concentration reaches 1% (w/v), and is difficult to dissolve in water due to its aggregability. The viscosity increases when ethyl alcohol is added to *Aureobasidium* β-glucan 0.1% (w/v) aqueous solution, and a jelly form results. Given that β-glucans are difficult to dissolve in water and alcohols and has a high viscosity, they have been extremeley difficult to handle when used as a flocculant, food modifier, supplement, or the like.

In addition, the rate of digestion and absorption is low even when β-glucans are taken as a supplement due to its extremely high molecular weight. Hydrolysis to a molecular weight more readily absorbed in the gastrointestinal tract is necessary to increase the digestion/absorption rate. However, because low molecular weight β-glucans are predicted to have reduced physiological activity, the development of technology to hydrolyze the saccharides while providing an immunopotentiating effect and cancer-suppressing effect was desired. There are methods of degradation using enzymes to produce the desired molecular weight, but *Aureobasidium* β-glucan could not be enzymatically decomposed at all when it was extracted from the culture broth.

β-Glucans exist as a triple-chain triple helical structure in nature, but the sugar chains can be cleaved by chemical hydrolysis through the use of an acid, alkali, or the like. Usually the triple chain is cleaved by hydrolysis without further modification, but triple-chain β-glucans can also sometimes be made into single-chain β-glucans, depending on the conditions. In addition, making a triple-chain β-glucan into a single chain has been shown to obtain a greater effect on the immunopotentiating effect and the like.

Non-patent Document 1 discloses the activity depending on differences in the structure of *schizophyllan* produced by *Schizophyllum commune*. Non-patent Document 2 comparatively studies the structure and physiological activity of various β-glucans and conducts studies using alkali-treated *schizophyllan* as a single-chain β-glucan. *Schizophyllan* is a β-glucan known to have antitumor activity, and goes from a triple helical structure to a single-chain random structure due to organic solvents such as dimethyl sulfoxide and alkaline conditions of pH 13 and higher. Non-patent Documents 1 and 2 show higher nitric oxide (NO) synthesis in vivo when *schizophyllan* is made into a single chain by alkali treatment in comparison to triple-chain *schizophyllan,* and disclose not only potentiated expression of interferon γ but also potentiated NO synthesis and increased expression of interleukin 1-α, interleukin-6, and TNF-α in vivo.

In addition, since making a β-glucan into a single chain decreases the molecular weight, the viscosity decreases, the solubility improves, and it is expected to become easier to handle. Since treatment by glycolytic enzymes becomes easier when the solubility improves, not only can the digestion/absorption rate be expected to increase, but processing is expected to be facilitated when used as a food additive or supplement.

In addition, laminarioligosaccharide obtained by enzymolysis of β-glucans is reported to act to protect against HIV virus infection when chemically modified and is expected to find use as a pharmaceutical raw material (Non-patent Document 3). A technique to prepare single-chain β-glucans is desired since single-chain β-glucans exhibit higher effects, as was mentioned above.

Although not a technique for making β-glucans into a single chain, methods for lowering the viscosity of β-glucans by conducting hydrothermal treatment under high-temperature, high-pressure conditions have been disclosed recently (Patent Documents 1 and 2). Patent Document 1 discloses that a low-viscosity solution is obtained by hydrothermal treatment of β-glucan aqueous solution obtained from *Aureobasidium* for a predetermined length of time at a pressure of 0.5-2.0 MPa and a temperature higher than 140° C. in a temperature range not exceeding 200 C., which is a state pressurized above the saturated water vapor pressure at the treatment temperature.

In addition, Patent Document 2 discloses that low-molecular β-glucans are extracted from *Ganoderma lucidum* cells by pressurized hot water. According to the content of Patent Document 2, (1,3)(1,6)-β-glucan, which is a constituent sugar of the cell walls of the cells, is hydrolyzed, solid *Ganoderma lucidum* into contact with pressurized hot water;

the molecular weight is lowered to a level allowing dissolution in water, and extraction is possible.

PRIOR ART DOCUMENTS

Non-Patent Documents

[Non-patent Document 1] Ohno, N., et al., 1996, Immunology Letters, Vol. 53, p. 157-163

[Non-patent Document 2] Toshiro Yadomae, Yakugaku Zasshi, 2000, Vol. 120(5), p. 413-431.

[Non-patent Document 3] Uryu, T., et al., Biochemical Pharmacology, 1992, Vol. 43, p. 2385-2392.

[Non-patent Document 4] Sato, T., et al., Polym. J., 1983, Vol. 15, p. 87-96.

[Non-patent Document 5] T. M. McIntire & D. A. Brant, J. Am. Chem. Soc., 1998, Vol. 120, p. 6909-6919.

[Non-patent Document 6] Nagi, N., et al., Biol. Pharm. Bull., 1993, Vol. 16(9), p. 822-828.

Patent Documents

[Patent Document 1] JP 2011-103877
[Patent Document 2] JP 2008-138195

SUMMARY OF THE INVENTION

Problem to be Solved by the Invention

The problem addressed by the present invention is to obtain a composition that contains single-chain β-glucans in a high concentration and has a lowered viscosity. This is because not only can potentiation of the strong immunopotentiating effect and antitumor effect be expected by producing single-chain β-glucans, but β-glucans of a viscosity that is easy to handle as a general food or food additive can be produced.

Chemical treatment methods involving an acid, alkali, or the like exist as described above as methods for producing single-chain β-glucans. However, considering use as a general food, food additive, or supplement, chemical treatment using an acid, alkali, or an organic solvent such as dimethyl sulfoxide cannot be taken a preferred treatment method because the possibility of generating new compounds cannot be denied. There is also a need for neutralization and removal of chemicals after treatment in the case of chemical treatment using acid or alkali. The need to remove chemicals also arises when an organic solvent is used. Thus, conducting chemical treatment requires many steps and involves problems such as not only the cost of chemicals and the like but also the removal and disposal of the chemicals used in the treatment process.

In addition, even if a single-chain β-glucan is obtained by alkali treatment or addition of an organic solvent, it is reported to revert to a triple-chain β-glucan during storage when treatment is conducted by neutralization or dialysis (Non-patent Documents 4 and 5). Therefore, the stability is low and only a product with a short shelf life can be produced even to be used as a food or supplement.

Hydrothermal treatment which is known as a method for lowering the viscosity of β-glucans is far superior in terms of safety because it does not use chemical products. However, since treatment is conducted using the decrease in viscosity as the indicator, the state of the β-glucan as the molecular weight decreases is unclear. Specifically, there is a risk that the molecular weight decreases while the β-glucan remains a shortened triple chain. Even if shortened triple-chain β-glucans were obtained, one could not expect potentiation of the antitumor activity or immunopotentiating activity.

Furthermore, it is necessary to produce a constant amount of β-glucans industrially to provide single-chain β-glucans to be contained in foods and cosmetics. Nonetheless, the method of Document 1 is a laboratory-level treatment method and could only treat a small amount of β-glucans. It was therefore necessary to study continuous treatment methods. In fact, when a slurry for hydrothermal treatment was prepared using the method of Document 1, it solidified, could not be supplied continuously to the hydrothermal treatment apparatus, and hydrothermal treatment could not be conducted. Therefore, it was necessary to study the slurry preparation conditions to produce single-chain β-glucans by hydrothermal treatment.

A problem addressed by the present invention is to produce a liquid composition containing single-chain β-glucans in a high concentration suited to ingestion as a general food, food additive, supplement, or the like as well as to produce a β-glucan composition that can be stored for an extended period of time while maintaining a single-chain state.

Means for Solving the Problems

The present invention relates to a β-glucan composition and a method for producing said composition and to a liquid composition containing said β-glucan composition to solve the above problems.

(1) A method for producing single-chain (1,3)(1,6)-β-glucan wherein the production method is characterized in that a solution containing (1,3)(1,6)-β-glucan is hydrothermally treated for a predetermined time in a temperature range of from 145° C. to 200° C. at a pressure at or above the saturated vapor pressure at the treatment temperature.

(2) The production method of (1) wherein the temperature range is from 145° C. to 190° C.

(3) The production method of (1) or (2) wherein the temperature range is from 145° C. to 180° C.

(4) The production method of any of (1)-(3) wherein the solution containing (1,3)(1,6)-β-glucan is a high-viscosity culture broth of black yeast of the genus *Aureobasidium*.

(5) The production method of any of (1)-(4) wherein the solution containing (1,3)(1,6)-β-glucan is adjusted to a pH higher than 2.0 and lower than 6.0 prior to hydrothermal treatment.

(6) The production method of (5) wherein the solution containing (1,3)(1,6)-β-glucan is adjusted to a pH of from 2.3 to 5.5 prior to hydrothermal treatment.

(7) A single-chain β-glucan composition having long-term storage stability characterized in that 70% or more of the total amount of (1,3)(1,6)-β-glucan are single-chain β-glucans.

(8) The single-chain β-glucan composition of (7) characterized in that the (1,3)(1,6)-β-glucan is (1,3)(1,6)-β-glucan produced by black yeast of the genus *Aureobasidium*.

(9) A single-chain β-glucan composition having long-term storage stability obtained by hydrothermal treatment of a solution containing (1,3)(1,6)-β-glucan for a predetermined time in a temperature range of from 145° C. to 200° C. at a pressure at or above the saturated vapor pressure at the treatment temperature.

(10) A liquid composition containing the single-chain β-glucan composition of any of (7)-(9) wherein the liquid composition is characterized by being a supplement beverage, liquid cosmetic, or liquid quasi-drug.

Effect of the Invention

It became possible to produce a composition containing single-chain β-glucans in a high concentration that is highly safe even when added to foods and supplements. In addition, the single-chain β-glucan composition produced by the production method of the present invention can be stored for an extended period of time because it has high storage stability.

BEST MODE FOR CARRYING OUT THE INVENTION

Figure 1:
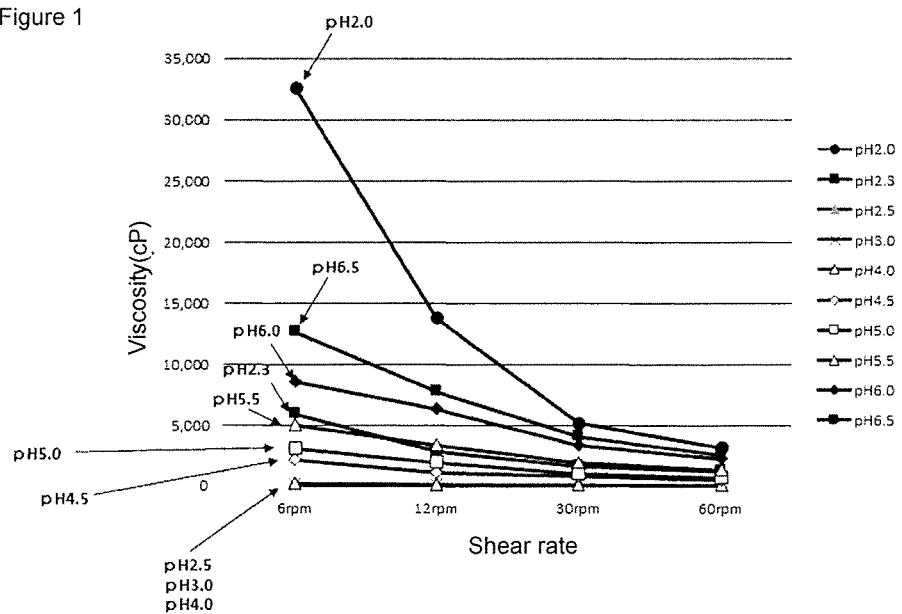
FIG. 1 Changes in the slurry depending on pH.

The present inventors conducted in-depth studies with the thought that there might be a temperature range within which triple-chain β-glucan is degraded into single-chain β-glucan by proper hydrothermal treatment. As a result, it became clear that a composition containing 70% or more single-chain β-glucan is obtained by treatment for a predetermined length of time within a temperature range of from 145° C. to 200° C.

When treated at a high temperature; i.e., above 200° C., the sample turns brown severely and is unsuitable for addition to foods. Based on the rate of degradation by enzymatic treatment, there is concern about the degradation rate when treated at temperatures higher than 190° C. Therefore, hydrothermal treatment at 190° C. or lower is preferred, and hydrothermal treatment at 180° C. or lower is more preferred in consideration of the efficiency of enzymatic treatment. In addition, virtually no browning occurs if treatment is conducted at a temperature of 170° C. or lower, and single-chain β-glucan is contained in a high concentration of 70% or more.

Therefore, a composition having high enzymatic treatment efficiency in which 70% or more is single-chain β-glucan can be obtained by hydrothermal treatment in a temperature range of from 145° C. to 200° C., preferably from 145° C. to 190° C., and more preferably from 145° C. to 180° C.

The time necessary for hydrothermal treatment is preferably from 10 minutes to less than 60 minutes. A decrease in the proportion of single-chain β-glucan produced is a possibility with times shorter than 10 minutes at any treatment temperature. In addition, browning occurs with treatment times longer than 60 minutes, leading to unsuitability as a general food or food additive.

In addition, it became clear that the pH is important when suspending the pressed product of the yeast culture broth which is the raw material when producing single-chain β-glucans on an industrial production scale. If the pH is not weakly acidic, a slurry will not form but a solid structure will, it becomes impossible to supply a continuous hydrothermal treatment apparatus, and hydrothermal treatment cannot be conducted.

The single-chain yeast β-glucan composition of the present invention is very easy to handle because of the high water solubility and low viscosity. In addition, since the aqueous solution is transparent and tasteless, the composition does not interfere with materials with which the solution is mixed. It can therefore be expected to be added to foods such as general foods, health foods, and supplements and to cosmetics and quasi-drugs to impart an immunopotentiating function. In addition, given that the aqueous solution has good solubility in water, it can be added in various forms such as an aqueous solution, powder, solid, or jelly. Furthermore, single-chain β-glucans produced within the temperature ranges shown below are stable even with long-term storage in an aqueous solution and can maintain a single-chain state. Therefore, these single-chain β-glucans have higher storage stability than single-chain β-glucans produced by chemicals such as alkalis and can maintain a single-chain state even when added to drink-like and jelly-like foods or to cosmetics and quasi-drugs.

These single-chain β-glucans can be added suitably to general foods such as candies, baked goods, chocolate, noodles, and cereals, beverages such as mineral water, tea, coffee, juice, green vegetable juice, and other such soft drinks, alcoholic beverages, and the like. In addition, the form of a single-chain β-glucan can be maintained stably over an extended period of time even when added to various forms of supplements. The single-chain β-glucans can also be admixed with not only foods for humans, but also with feeds for pets. All can be expected to function to potentiate immunity. Single-chain β-glucans can also be added suitably to cosmetics such as cosmetic lotions, milky lotions, moisturizing lotions, hand creams, and shampoos and to quasi-drugs such as mouthwash and toothpaste.

Furthermore, it became clear that the single-chain β-glucans obtained by hydrothermal treatment are stable over an extended period of time either as an aqueous solution or a powder. It is known that 70% or more of single-chain β-glucans produced by alkali treatment revert to triple-chain β-glucans in about one week and becomes highly viscous. It was therefore difficult to supply products that function as single-chain β-glucans stably in the past. In contrast, when single-chain β-glucans was made by hydrothermal treatment, there was virtually no change in the proportion of single-chain β-glucan for one year or more, even in solution. Therefore, it becomes possible to supply products that maintain their potency and are stable over an extended period of time even when β-glucan is contained in beverages or solutions such as cosmetic lotions.

Here, the storage stability of the single-chain β-glucans means that 70% or more is present in the form of single-chain β-glucans for at least one week. Preferably, 70% or more is present in the form of single-chain β-glucans for one month or longer, more preferably three months or longer, and even more preferably six months or longer.

[Hydrothermal Treatment Apparatus]

Any apparatus may be used as a hydrothermal treatment apparatus as long as it is capable of pressurization and heating. A high-temperature and high-pressure apparatus, high-temperature and high-pressure reaction test apparatus, and the like can be used. Specifically, a single-pass (batch type) subcritical water reactor or a continuous subcritical water reactor capable of conducting hydrothermal treatment continuously can be used. Examples include an EMI-SYSTEM (manufactured by Techno-EMI Co.), a hydrothermal synthesis/degradation apparatus (manufactured by AKICO Co.), a tube reactor-type hydrothermal reactor (manufactured by Kimura Kako Co., Ltd.), and the like.

[Raw Material]

Cereals such as barley and oats, the fruiting bodies or culture broth of *Lentinus edodes, Schizophyllum commune, Coriolus versicolor, G. frondosa, Sparassis crispa*, and the like, the culture broth of baker's years or beer yeast, and the like may be used as the β-glucan raw material. The explanation here uses a highly viscous culture broth obtained by culturing the black yeast, *Aureobasidium pullulans*, but of course not only the culture broth of *Aureobasidium pullulans*, but also the culture broth of other yeasts and raw materials known to produce β-glucans can also be used suitably in the same way.

The culture broth contains about 0.5% (1,3)(1,6)-β-glucan, cells, and fermentation residue. Since this culture broth contains polysaccharides including β-glucans released by the *Aureobasidium* into the culture broth, it has an extremely high viscosity like that of a raw egg white. The culture broth of *Aureobasidium* may be used as it is, or a pressed product obtained by the following method may be used.

When the *Aureobasidium* culture broth is used as a pressed product, a flocculant is added to the culture broth to produce flocs. The flocs are pressed by a filter press, the fermentation residue and cells are removed, and pressing and filtration may be performed. Specifically, aluminum sulfate solution is added to the *Aureobasidium* culture broth to make a final concentration of 0.1% and insoluble polysaccharide-aluminum complexes are formed. The polysaccharide-aluminum complexes are slowly stirred for 30-60 minutes at room temperature. The polysaccharide-aluminum complexes formed are introduced into a filter press, and the fermentation residue and cells are washed and removed by passage of tap water to obtain a pressed product. The fermentation residue and cells are basically removed by pressing-filtration treatment, and a polysaccharide-rich pressed product having a water content of 65-80% is obtained.

The method for producing single-chain β-glucan of the present invention is explained in detail below through examples.

1. Method for producing single-chain β-glucan

EXAMPLE 1

(1) Method for preparing hydrothermal treatment sample (preparation method for a small-scale sample)

Two hundred grams of *Aureobasidium* pressed product (wet weight, solids content 20%) was taken, 720 mL of distilled water was added, and the mixture was pulverized in a mixer. Once the pressed product had been pulverized well, 80 mL of 1N NaOH was added and stirred well using a stirrer. The final NaOH concentration of the pulverized solution was 0.1N. The stirred sample was centrifuged for 10 minutes at 6000 rpm, and the supernatant was recovered. A two-fold quantity of anhydrous ethanol was added to the recovered supernatant to precipitate it. Since β-glucans are precipitated by ethanol, the precipitate was filtered and recovered, and the ethanol was evaporated off over one hour in a 60° C. oven. Distilled water was again added to dissolve the precipitate from which the ethanol had been evaporated off, and the β-glucans were recovered. The recovered β-glucans were diluted with distilled water to make 0.35% (w/v) and adjusted to pH 6.0 by 1N HCl or 1N NaOH. The pH-adjusted sample was placed in a hydrothermal reactor, heated to the predetermined temperature in the 110-190° C. temperature range, and reacted for 10 minutes at each temperature. The pressure during reaction at this time was 0.5-2.0 MPa.

EXAMPLE 2

(2) Method for preparing hydrothermal treatment sample (preparation method for sample for continuous production)

Hydrothermal treatment is conducted continuously when producing single-chain β-glucans industrially. When subjecting a pressed product to hydrothermal treatment continuously, the slurry for hydrothermal treatment must have fluidity. Since it was clear that the state of the slurry changes during production depending on the pH, the pH during slurry preparation was analyzed.

Fifty grams of culture pressed product was pulverized in 1100 mL of water, and a slurry was produced. The β-glucan concentration at this time was estimated to be about 2% (w/v). Furthermore, the β-glucans were prepared to be about 2% (w/v) here, but may be prepared to a concentration range of about 1-5% (w/v). Next, the pH was adjusted to 2.0-6.5 using 1N NaOH, and the changes in the slurry were analyzed. After the pH-adjusted slurry had stood for one hour, the viscosity was measured using a Brookfield viscometer (manufactured by Tokyo Keiki Seisakusho Co., Ltd.) (FIG. 1).

When allowed to stand at pH 2.0 or pH 6.0 or above, the slurry solidified completely. Therefore, the conditions must be a pH higher than 2.0 and lower than pH 6.0. Since the slurry had fluidity despite its high viscosity when the pH was 2.3 or 5.5, it is preferable to adjust the pH of the slurry to a pH from 2.3 to 5.5.

A slurry that has been adjusted to a pH from 2.3 to 5.5 can be subjected to hydrothermal treatment continuously. In addition, it was understood that excessive degradation of the β-glucan occurs and the recovery rate decreases when the pH is lower than 3.0 during the hydrothermal reaction. Therefore, it is more preferable to adjust the pH to a pH range from 3.0 to 5.5 during slurry preparation and to conduct hydrothermal treatment. A sample having the pH adjusted to this range is introduced continuously into an apparatus capable of a hydrothermal reaction and heated for a predetermined length of time in a temperature range of 145-190° C. Furthermore, the pressure during the reaction at this time is 0.5-2.0 MPa.

Moreover, high-purity single-chain β-glucans can be obtained if the β-glucans are purified as follows after hydrothermal treatment. The reaction residue is removed by filtering the treated solution after the hydrothermal reaction. The filtrate may be recovered by a common filtration method such as reduced-pressure filtration, pressurized filtration, or centrifugal filtration.

The recovered filtrate is concentrated if necessary. A method such as freeze drying or ultrafiltration may be used in concentration. If ultrafiltration is used, one can select a cross-flow method, full-flow method, or the like, and the cross-flow method can be carried out using a module such as an organic membrane, ceramic, or the like. If ultrafiltration is used, ultrafiltration-concentration is conducted with a molecular weight of about 30,000 or lower as the exclusion molecular weight, and the low-molecular-weight sugars are removed. Crude purification can be conducted simultaneously with concentration. Concentration at this time should be confirmed using a Brix meter. Here, concentration of the solids fraction concentration of the concentrated solution was confirmed with Brix going from 1% to 5% by Brix meter (manufactured by Atago Co., Ltd., Brix meter PAL). Freeze drying is conducted thereafter, and a high-purity powder can be obtained by pulverization.

EXAMPLE 3

(3) Method for measuring proportion of single-chain β-glucans

Single-chain glucans and triple-chain glucans can be distinguished by a Limulus test. β-Glucans that had been hydrothermally treated at each temperature using hydrothermal treatment samples prepared in Example 1 were therefore measured by a Limulus test, and the proportion of single-chain β-glucan was determined. The control single-chain glucans were obtained by dissolution in 0.5N NaOH (Non-patent Document 6). Furthermore, about the same proportion of single-chain glucan was produced when hydrothermal treatment was conducted continuously as in Example 2 and when hydrothermal treatment was conducted on a small scale as in Example 1.

Glucans that have been dissolved by alkali become single-chain and can be distinguished from triple-chain β-glucans by the Limulus test, as mentioned above. β-Glucans that had been alkali treated by 0.5N NaOH were taken as β-glucans 100% degraded into single-chain. β-Glucan samples that had not been alkali treated were taken to contain no single-chain forms and were mixed with alkali-treated β-glucan in predetermined proportions, and a Limulus test calibration curve was produced.

Specifically, β-glucan samples for the Limulus test were prepared as follows. β-glucans recovered by ethanol precipitation from a pressed product in the same way as described above was diluted as appropriate by water, then freeze dried and powdered. β-Glucans in this state are triple-chain β-glucans. These β-glucans are referred to as untreated β-glucans below.

Next, untreated β-glucans that had been powdered by freeze drying was dissolved by 0.5N NaOH to make 10 mg/mL. These become single-chain β-glucans due to dissolution by 0.5N NaOH. The dissolved single-chain β-glucans were dialyzed for one day against distilled water, again freeze dried and powdered, and recovered. Despite being alkali-treated, the β-glucan can be stored while maintaining a single chain by being stored in a freeze-dried state.

For the hydrothermal treatment samples, untreated β-glucans were subjected to hydrothermal treatment at each temperature by the method of Example 1, then dialyzed for one day against distilled water, freeze dried, and recovered.

The samples to be measured were all adjusted to 10 mg/mL, then diluted to $10^{-7}$ g/mL. A calibration curve was produced by mixing alkali-treated single-chain β-glucans with untreated β-glucan (triple-chain β-glucans) to make 100%, 80%, 40%, 20%, and 0%.

Otsuka distilled water (for injection, manufactured by Otsuka Pharmaceutical Co., Ltd.) was used as the diluting water used in measurement. In addition, all of the equipment such as the tubes used was pyrogen-free. All test procedures were also conducted in a clean room. The Limulus test was conducted using a Glucatell with Pyrocolor DIA60-STV (both manufactured by Biochemical Biobusiness) as the chromogenic reagent. For the measuring, the 540 nm absorbance was measured using an absorption spectrometer (manufactured by Hitachi High-Tech Science Co., Ltd.). The proportion of single-chain in β-glucans treated at each treatment temperature was calculated based on the calibration curve. The results are shown in Table 1.

TABLE 1

| | Treatment temperature | | | | | | |
|---|---|---|---|---|---|---|---|
| | Un-treated | 140° C. | 145° C. | 150° C. | 170° C. | 180° C. | 190° C. |
| Proportion of single-chain | 4% | 7% | 77% | 93% | 98% | 103% | 99% |

As shown in Table 1, the sample hydrothermally treated at 140° C. contained only 7% single-chain β-glucans, virtually unchanged from the untreated sample. In contrast, the sample hydrothermally treated at 145° C. was 77% single-chain β-glucans. Moreover, samples hydrothermally treated at temperature of 150° C. and above all contained 90% or more single-chain β-glucans.

Therefore, 70% or more of the β-glucans in the composition is believed to become single-chain β-glucans if hydrothermally treated at a temperature of 145° C. or higher. Hydrothermal treatment at a temperature higher than 145° C. is believed to make triple-chain β-glucans into single-chain β-glucans, but browning of the sample is severe when treated at a high temperature of 200° C. or above. Virtually no browning occurs if treated at a temperature of 190° C. or less. In addition, hydrothermal treatment in a temperature range of from 145° C. to 190° C. is preferable so that a high concentration of 70% or more single-chain β-glucans is contained.

EXAMPLE 4

Relationship between proportion of single-chain β-glucans and enzymatic reaction Degradation to a certain extent to a lower molecular weight to allow the product to be contained in foods and supplements is preferred because of the high molecular weight and low absorption efficiency from the intestine. However, triple-chain β-glucans do not undergo a degradation reaction by virtually any enzymes. Therefore, we analyzed whether single-chain β-glucans are degraded by enzymes.

β-Glucan samples hydrothermally treated in the same way as above and untreated β-glucans were adjusted to pH 6.0 by dilute HCl or dilute NaOH, and diluted to a concentration of 3.5 mg/mL. Hydrothermal treatment was conducted at temperatures every 10° C. from 110° C. to 190° C. For glycolytic enzyme, Lysing Enzyme (from Trichoderma harzianum, manufactured by Sigma-Aldrich) was dissolved in a concentration of 40 mg/mL, and 0.8 mg of crude enzyme was added per milligram of β-glucan sample. Distilled water was used for background measurement. An enzymatic reaction was carried out at 40° C., and samples were taken every six hours up to 30 hours. The samples collected were diluted ten-fold by distilled water, and the enzymatic reaction was stopped by boiling for 10 minutes.

Figure 2:
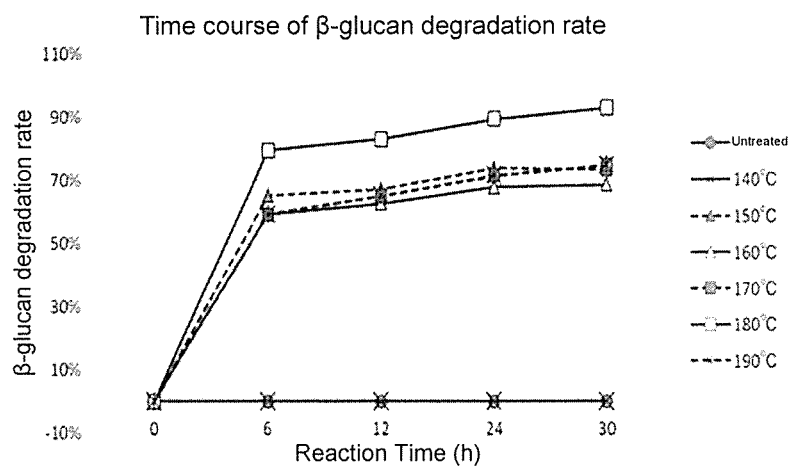
FIG. 2 Relationship between temperature and the rate of degradation by enzymes.

Analysis was performed by HPLC. Analysis was performed using a Shodex KS-801 column (manufactured by Showa Denko K. K.) at 60° C., a flow rate of 0.5 mL/min, and using ultrapure water as the solvent. The degradation rate was evaluated by the decrease relative to the peak height of the β-glucans at the start of the reaction. The results are shown in FIG. 2.

It was confirmed that virtually no degradation occurs even with long-term treatment by enzymes and triple-chain β-glucans are not enzymatically degraded at hydrothermal treatment temperatures of 140° C. and below. On the other hand, efficient sugar degradation occurred such that 90% or more became single-chain β-glucans at hydrothermal treatment temperatures of 150° C. and above. Although virtually no difference in degradation efficiency was seen from 150° C. to 170° C., very efficient degradation by enzymes occurred at a hydrothermal treatment temperature of 180° C. The degradation efficiency in 190° C. hydrothermal treatment was equivalent to that at 150 and 170° C. The β-glucans are believed to become completely single-chain in the 190° C. temperature zone, but it is assumed that many excessive degradation products derived from β-glucans are produced in the course of hydrothermal treatment, and that these interfere with the enzymatic reaction.

Based on the above results, it became clear that the degradation efficiency by enzymes correlates with the β-glucan structure. In other words, the β-glucan structure being a single chain contributes to the degradation efficiency by enzymes, and excessive degradation products due to further heating are thought to inhibit the enzymatic reaction. Therefore, we concluded that hydrothermal treatment at a temperature of 145° C. or higher is preferred when conducting enzymatic treatment using single-chain β-glucans, and hydrothermal treatment at a temperature of 180° C. or lower is more preferred from the viewpoint of enzymolysis efficiency in particular.

EXAMPLE 5

Long-term storage stability of single-chain β-glucans

It has been pointed out that single-chain β-glucans produced by alkali treatment reverts to triple-chain during storage when neutralized by acid or dialyzed. β-Glucans that have reverted to the triple-chain structure cannot be expected to have the potent immunopotentiating activity seen in single-chain β-glucans. Therefore, the long-term stability of single-chain β-glucans is an important problem. Consequently, single-chain β-glucans were produced by hydrothermal treatment, stored for an extended period of time, and the stability was analyzed.

The daily recommended intake of β-glucans is said to be about 30 mg. Therefore, a 50-mL drink that contained 30 mg of β-glucans (erythritol 16%, β-glucan concentration 0.06%, acidulant 0.5%, flavoring 0.3%) was produced, and the proportion of single-chain was measured after long-term storage.

The single-chain proportion was measured by the Limulus test using samples obtained by storing the above drink containing hydrothermally-treated (170° C., reaction time 15 minutes) β-glucans in a concentration of 0.06% for a year and a half and, as a control, the drink solution immediately after the β-glucans was added. The results are shown in Table 2.

TABLE 2

|  | Proportion |
|---|---|
| Immediately after adding β-glucan (production) | 84% |
| Samples stored for a year and a half | 84% |

The proportion of single-chain forms was the same: 84%, in both samples stored for a year and a half and samples that had just been produced. It has been pointed out that β-glucans obtained by alkali treatment revert to triple-chain forms in about a week when stored in aqueous solution, but it became clear that β-glucans made into a single chain by hydrothermal treatment maintains the single-chain form even after long-term storage for a year and a half. In other words, β-glucans made into a single chain form by hydrothermal treatment and β-glucans made into a single chain form by alkali treatment do not differ in that they are both single-chain β-glucans, but there are believed to be some structural differences that cannot be identified at the present time.

The above results show that single-chain β-glucans obtained by hydrothermal treatment are stable over an extended period of time. The fact that single-chain β-glucans can be supplied stably as an aqueous solution in particular proves the stability of their quality even when added to supplements in the form of a drink and to beverages. Therefore, the single-chain form is maintained for an extended period of time when used as a supplement and the like and is shown to have high immunopotentiating activity and the like.

The invention claimed is:

1. A method for producing single-chain (1,3)(1,6)-β-glucan,
wherein a solution containing (1,3)(1,6)-β-glucan is adjusted to a pH higher than 2.0 and lower than 5.5, and then is hydrothermally treated for a predetermined time in a temperature range of from 145° C. to 200° C. at a pressure at or above the saturated vapor pressure at the treatment temperature.

2. The production method of claim 1, wherein the temperature range is from 145° C. to 190° C.

3. The production method of claim 1, wherein the temperature range is from 145° C. to 180° C.

4. The production method of claim 1, wherein the solution containing (1,3)(1,6)-β-glucan is a high-viscosity culture broth of black yeast of the genus Aureobasidium.

5. A β-glucan composition having long-term storage stability characterized in that 70% or more of the total amount of (1,3)(1,6)-β-glucan are single-chain β-glucans.

6. The β-glucan composition of claim 5 characterized in that the (1,3)(1,6)-β-glucan is (1,3)(1,6)-β-glucan produced by black yeast of the genus Aureobasidium.

7. A single-chain β-glucan composition having long-term storage stability obtained by adjusting pH value to be higher 2.0 and lower than 5.5 of a solution containing (1,3)(1,6)-β-glucan, and then performing a hydrothermal treatment of the solution for a predetermined time in a temperature range of from 145° C. to 200° C. at a pressure at or above the saturated vapor pressure at the treatment temperature.

8. A liquid composition containing the β-glucan composition of claim 5, wherein the liquid composition is a supplement beverage, liquid cosmetic, or liquid quasi-drug.

9. The production method of claim 2, wherein the solution containing (1,3)(1,6)-β-glucan is a high-viscosity culture broth of black yeast of the genus Aureobasidium.

10. The production method of claim 3, wherein the solution containing (1,3)(1,6)-β-glucan is a high-viscosity culture broth of black yeast of the genus Aureobasidium.

11. A liquid composition containing the single-chain β-glucan composition of claim 6, wherein the liquid composition is a supplement beverage, liquid cosmetic, or liquid quasi-drug.

12. A liquid composition containing the single-chain β-glucan composition of claim 7, wherein the liquid composition is a supplement beverage, liquid cosmetic, or liquid quasi-drug.

13. The β-glucan composition of claim 5, further comprising triple-chain β-glucan and degradative products as the remainder of the β-glucan composition other than the single-chain β-glucans.

14. The liquid composition of claim 8, wherein 70% or more of the total amount of (1,3)(1,6)-β-glucan exist as single-chain β-glucans for at least one and a half years.

15. The liquid composition of claim 8, wherein a single-chain β-glucan proportion maintains for at least one and a half years.

* * * * *